(12) United States Patent
Bucholz

(10) Patent No.: US 9,457,180 B2
(45) Date of Patent: Oct. 4, 2016

(54) ELECTRODE CLAMP

(71) Applicant: Saint Louis University, St. Louis, MO (US)

(72) Inventor: Richard D. Bucholz, Ladue, MO (US)

(73) Assignee: St. Louis University, St. Louis, MO (US)

( * ) Notice: Subject to any disclaimer, the term of this patent is extended or adjusted under 35 U.S.C. 154(b) by 0 days.

(21) Appl. No.: 13/709,673

(22) Filed: Dec. 10, 2012

(65) Prior Publication Data

US 2013/0150934 A1    Jun. 13, 2013

Related U.S. Application Data

(60) Provisional application No. 61/569,071, filed on Dec. 9, 2011.

(51) Int. Cl.
*A61N 1/05* (2006.01)
*A61B 19/00* (2006.01)

(52) U.S. Cl.
CPC ............ *A61N 1/0539* (2013.01); *A61N 1/0534* (2013.01); *A61B 2090/103* (2016.02)

(58) Field of Classification Search
CPC ............. A61N 1/0534; A61N 1/0539; A61B 2019/208
USPC .................................. 607/116, 129, 139, 175
See application file for complete search history.

(56) References Cited

U.S. PATENT DOCUMENTS

| | | | | |
|---|---|---|---|---|
| 5,464,446 | A * | 11/1995 | Dreessen et al. | 607/116 |
| 6,324,433 | B1 * | 11/2001 | Errico | 607/116 |
| 7,004,948 | B1 * | 2/2006 | Pianca et al. | 606/129 |
| 7,981,119 | B2 | 7/2011 | Lando et al. | |
| 2005/0182425 | A1 * | 8/2005 | Schulte et al. | 606/130 |
| 2009/0112327 | A1 * | 4/2009 | Lane et al. | 623/17.19 |
| 2009/0182351 | A1 * | 7/2009 | Malinowski | 606/142 |
| 2009/0187149 | A1 | 7/2009 | Nelson | |
| 2010/0268308 | A1 | 10/2010 | Rossby | |
| 2011/0034981 | A1 | 2/2011 | Schulte et al. | |

OTHER PUBLICATIONS

International Search Report for PCT/US2012/68753 dated Feb. 28, 2013, 4 pgs.
Written Opinion for PCT/US2012/68753 dated Feb. 28, 2013, 5 pgs.

* cited by examiner

*Primary Examiner* — William Levicky
(74) *Attorney, Agent, or Firm* — Senniger Powers LLP

(57) ABSTRACT

A clamp for clamping a brain electrode extending through a burr hole formed in a skull of a patient. The clamp includes a first retainer element having a flange extending around an outer end for engaging an outer table of the skull and a jaw extending across the inner end. The clamp includes a second retainer element shaped complementarily to the first retainer element. The second retainer element has a flange extending around an outer end for engaging the outer table of the skull and a jaw extending across the inner end for cooperating with the jaw of the first retainer to clamp the electrode. The clamp has a cap for maintaining the jaws of the first and second retainer elements in cooperation to clamp the electrode adjacent an inner table of the skull. The cap includes an opening for receiving the electrode to hold the electrode against movement.

12 Claims, 7 Drawing Sheets

ELECTRODE CLAMP

CROSS REFERENCE TO RELATED APPLICATION

This Application claims priority to U.S. Provisional Patent Application No. 61/569,071 filed Dec. 9, 2011, entitled, "Burr Hole Electrode Clamp", which is incorporated by reference in its entirety.

BACKGROUND

The present invention generally relates to a clamp, and more particularly, to an electrode clamp used for clamping an electrode in position in a burr hole in a skull of a patient.

Electrodes are increasingly used to stimulate specific parts deep within a patient's brain to reduce movement disorders such as those accompanying Parkinson's disease, or to change compulsive behaviors such as those accompanying obsessive compulsive disorders. Other applications of this technology are also actively being developed. Frequently, the electrodes are introduced into the brain through holes drilled into the skull, known as burr holes, created by an automatic perforator having a carefully controlled diameter (e.g., 14 mm).

Electrodes are frequently bent where they emerge from the burr holes to lay flat against the skull under the scalp, minimizing their visual perceptibility to others. Ultimately, the electrodes travel to generators, usually on the chest, that electrically stimulate the brain via the electrodes based on a predetermined protocol. The bend in these electrodes at the edge of the burr holes frequently has a small radius, making the electrodes prone to breakage, thereby rendering them useless. If the electrodes break, the process of inserting electrodes must be repeated. The electrodes are inserted in small targets deep within the brain. Thus, the procedure is delicate and tedious. Preferably, electrode failure is minimized to minimize the need for repeating the procedure. Accordingly, there is a need for a mechanism for securely attaching electrodes to the skull and preserving a suitably large electrode radius of curvature as it exits the skull.

SUMMARY

In one aspect, the present disclosure relates to a clamp for clamping a brain electrode extending through a burr hole formed in a skull of a patient. The clamp comprises a first retainer element having a shell extending between an outer end and an inner end opposite the outer end. A flange extends around the outer end for engaging an outer table of the skull and a jaw extends across the inner end. The clamp includes a second retainer element having a shell shaped complementarily to the first retainer element shell for insertion in the burr hole simultaneously with the first retainer shell. The second retainer element shell extends between an outer end and an inner end opposite the outer end. The second retainer element shell has a flange extending around the outer end for engaging the outer table of the skull and a jaw extending across the inner end for cooperating with the jaw of the first retainer to clamp the electrode. The clamp includes a cap having a recess for simultaneously receiving the flanges of the first retainer element and the second retainer element for maintaining the jaws of the first and second retainer elements in cooperation to clamp the electrode adjacent an inner table of the skull while the flanges of the first and second retainer elements engage the outer table of the skull. The cap includes an opening for receiving the electrode. The opening is positioned adjacent at least one of the flanges of the first and second retainer elements when the cap recess receives the flanges to hold the electrode against movement within the shells of the first and second retainer elements and maintain a curvature of the electrode during use.

In another aspect, the present disclosure relates to a clamp for clamping a brain electrode extending through a burr hole formed in a skull of a patient. The clamp comprises a first retainer element having a shell extending between an outer end and an inner end opposite the outer end. A flange extends around the outer end for engaging an outer table of the skull and a jaw extends across the inner end. The clamp includes a second retainer element having a shell shaped complementarily to the first retainer element shell for insertion in the burr hole simultaneously with the first retainer shell. The second retainer element shell extends between an outer end and an inner end opposite the outer end. The second retainer element shell has a flange extending around the outer end for engaging the outer table of the skull and a jaw extending across the inner end for cooperating with the jaw of the first retainer to clamp the electrode. The second retainer has a spacer extending across the inner end and overlying the first retainer element inner end when assembled. The clamp further comprises a cap fastened to the first and second retainer elements for maintaining the jaws of the first and second retainer elements in cooperation to clamp the electrode adjacent an inner table of the skull while the flanges of the first and second retainer elements engage the outer table of the skull. The cap includes an opening for receiving the electrode.

In yet another aspect, the present disclosure relates to a clamp for clamping a brain electrode extending through a burr hole formed in a skull of a patient. The clamp comprises a retainer assembly sized for insertion in the burr hole. The assembly has a clamp for clamping the electrode and a stop for positioning the clamp adjacent an inner table of the skull. The clamp also has a cap attachable to the retainer for covering the burr hole.

Other aspects of the present invention will be apparent in view of the following description and claims.

BRIEF DESCRIPTION OF THE DRAWINGS

Corresponding reference characters indicate corresponding parts throughout the drawings.

DETAILED DESCRIPTION OF THE DRAWINGS

Figure 1:
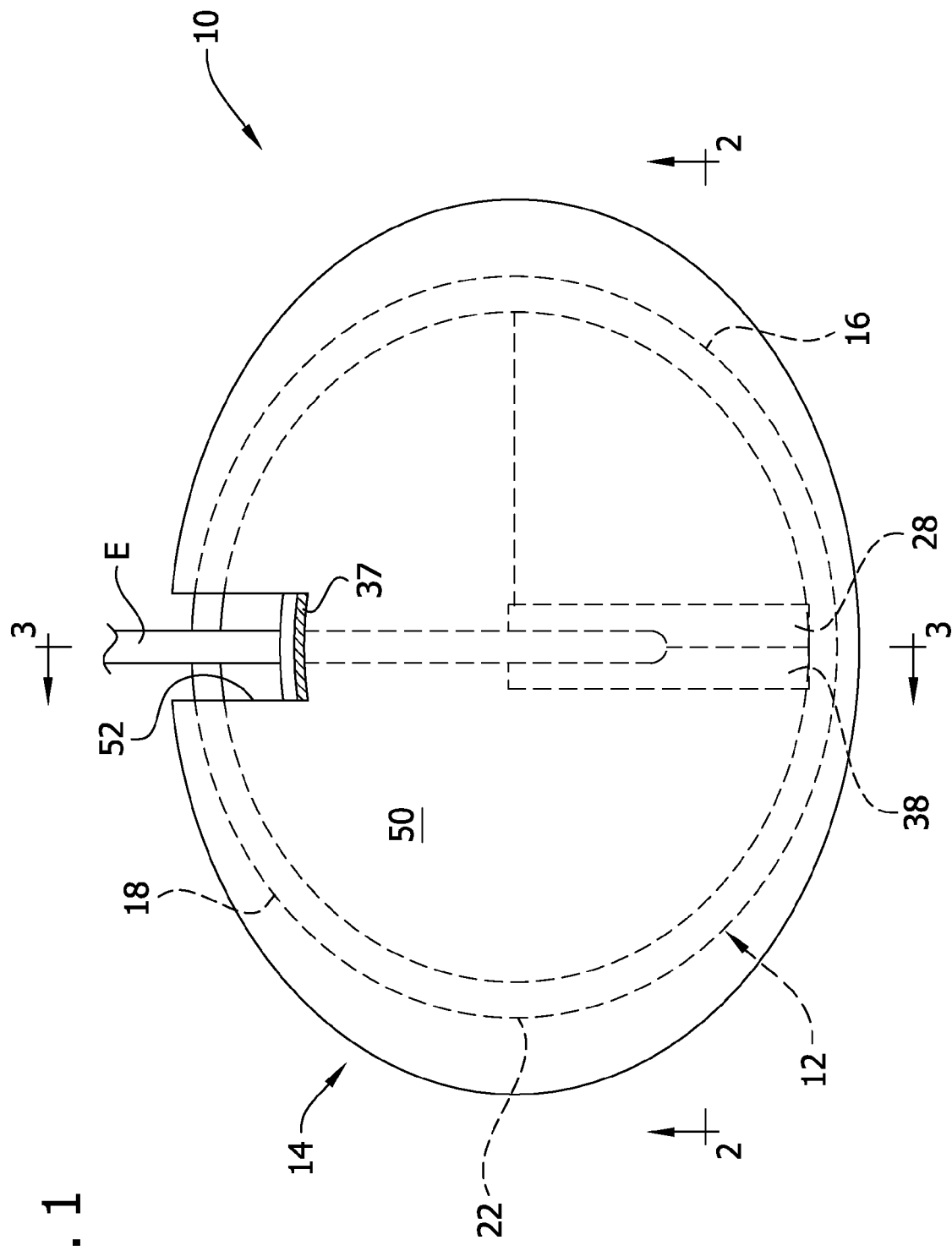
FIG. 1 is a top plan of an electrode clamp.
Figure 2:
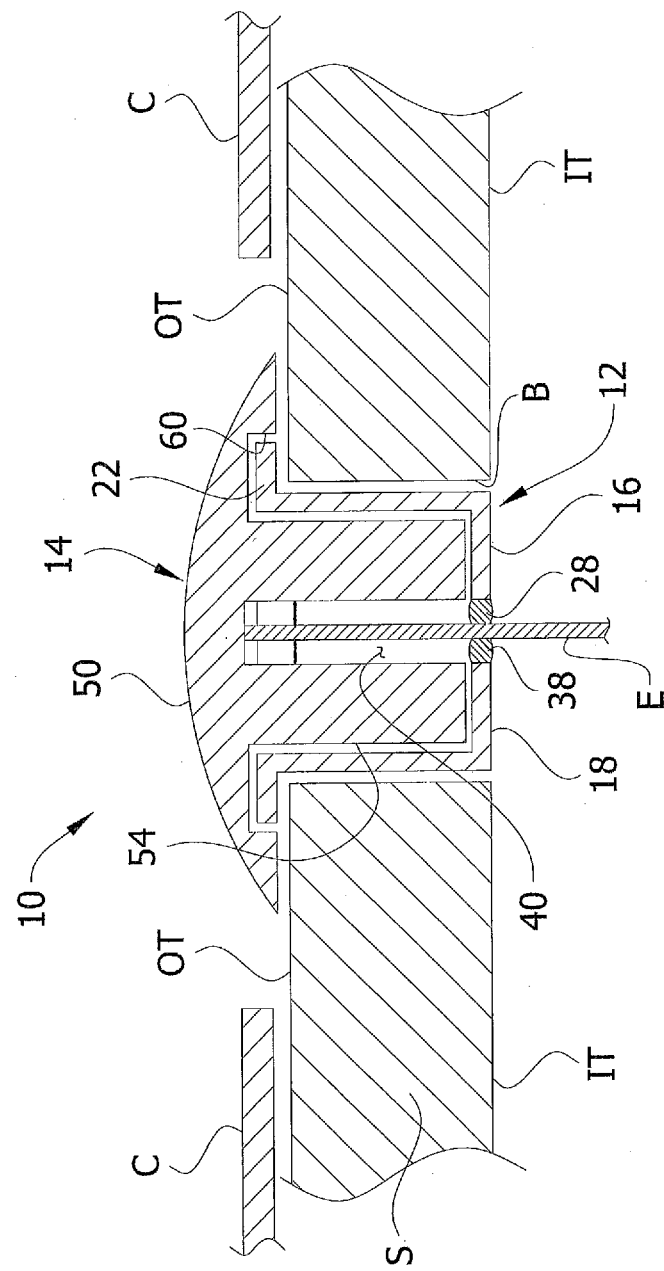
FIG. 2 is a cross section of the clamp taken in the plane of line 2-2 in FIG. 1.
Figure 3:
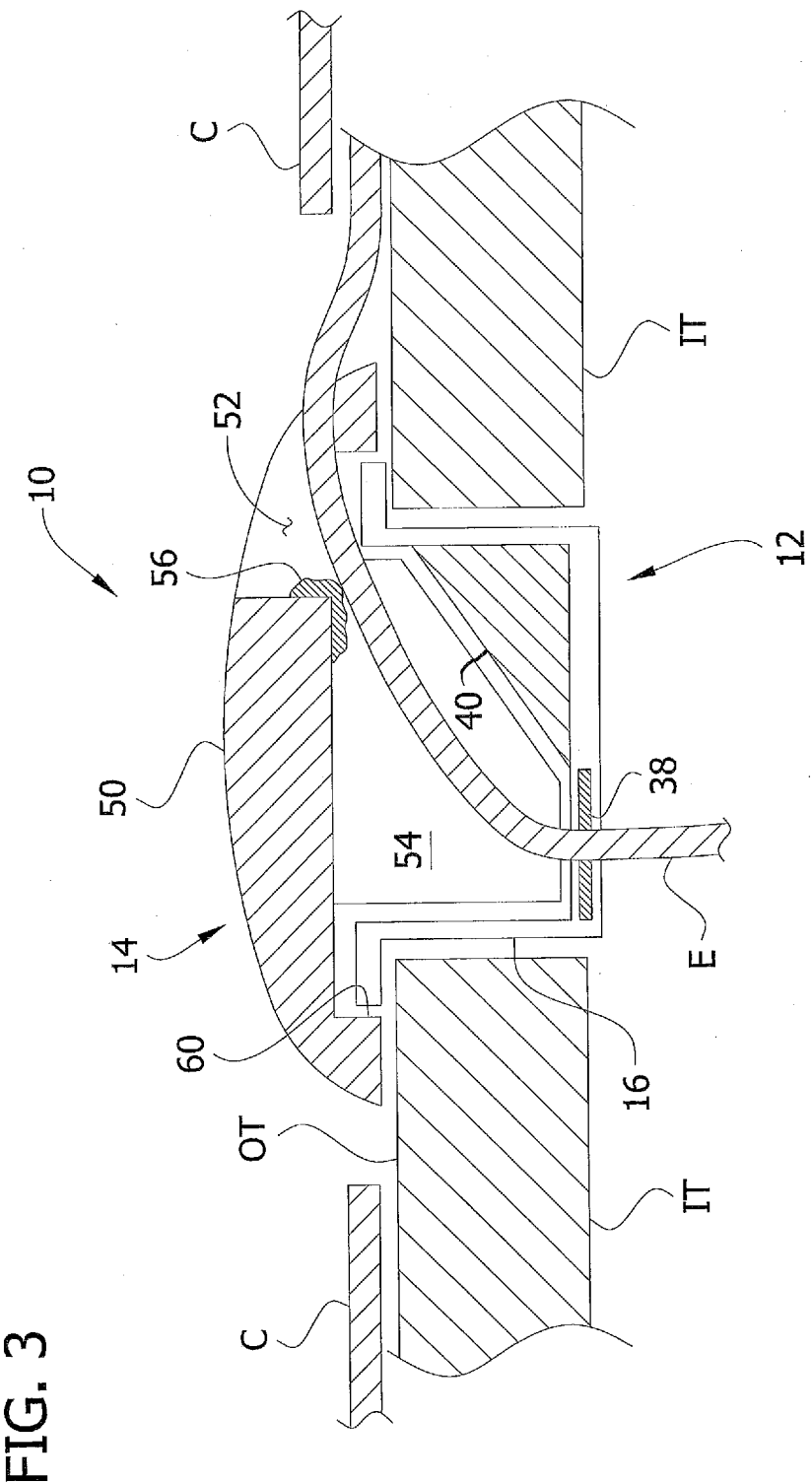
FIG. 3 is a cross section of the clamp taken in the plane of line 3-3 in FIG. 1.

Referring to FIG. 1, an electrode clamp or stabilizer for clamping a brain electrode E extending through a burr hole B (FIG. 2) formed in a skull S (FIG. 2) of a patient is designated in its entirety by the reference number 10. As illustrated in FIGS. 2 and 3, the stabilizer 10 comprises a retainer assembly, generally designated by 12, and a cap, generally designated by 14. The retainer assembly 12 clamps the electrode E in the burr hole B at an inner location adjacent an inner table IT of the skull S. The retainer assembly 12 and the cap 14 also clamp the electrode E at an outer location adjacent an outer table OT of the skull S. Between the inner location and the outer location, the clamp 10 allows the electrode E to bend in a generous arc that reduces potential for damaging the electrode. Further, the outer clamp preserves the generous arc during use. At the inner location, the electrode E enters the retainer assembly 12 generally perpendicular to the inner table IT of the skull S. As will become apparent, the clamp 10 is adapted to receive the electrode E regardless of the radial position at which it passes through the burr hole B. At the outer location, the electrode E exits the clamp 10 generally parallel to the outer table OT of the skull S, allowing the electrode to extend from the clamp beneath or adjacent to the scalp C of the patient.

Figure 4:
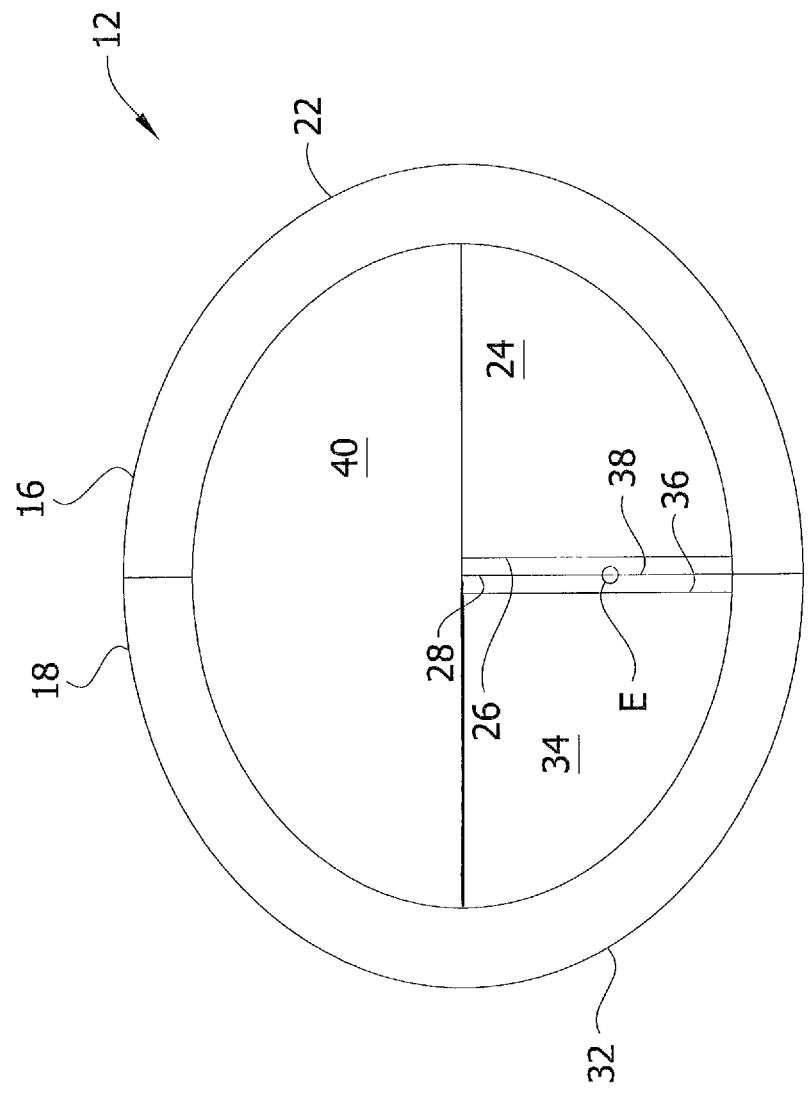
FIG. 4 is a top plan of a retainer assembly of the clamp having a cap removed.
Figure 5:
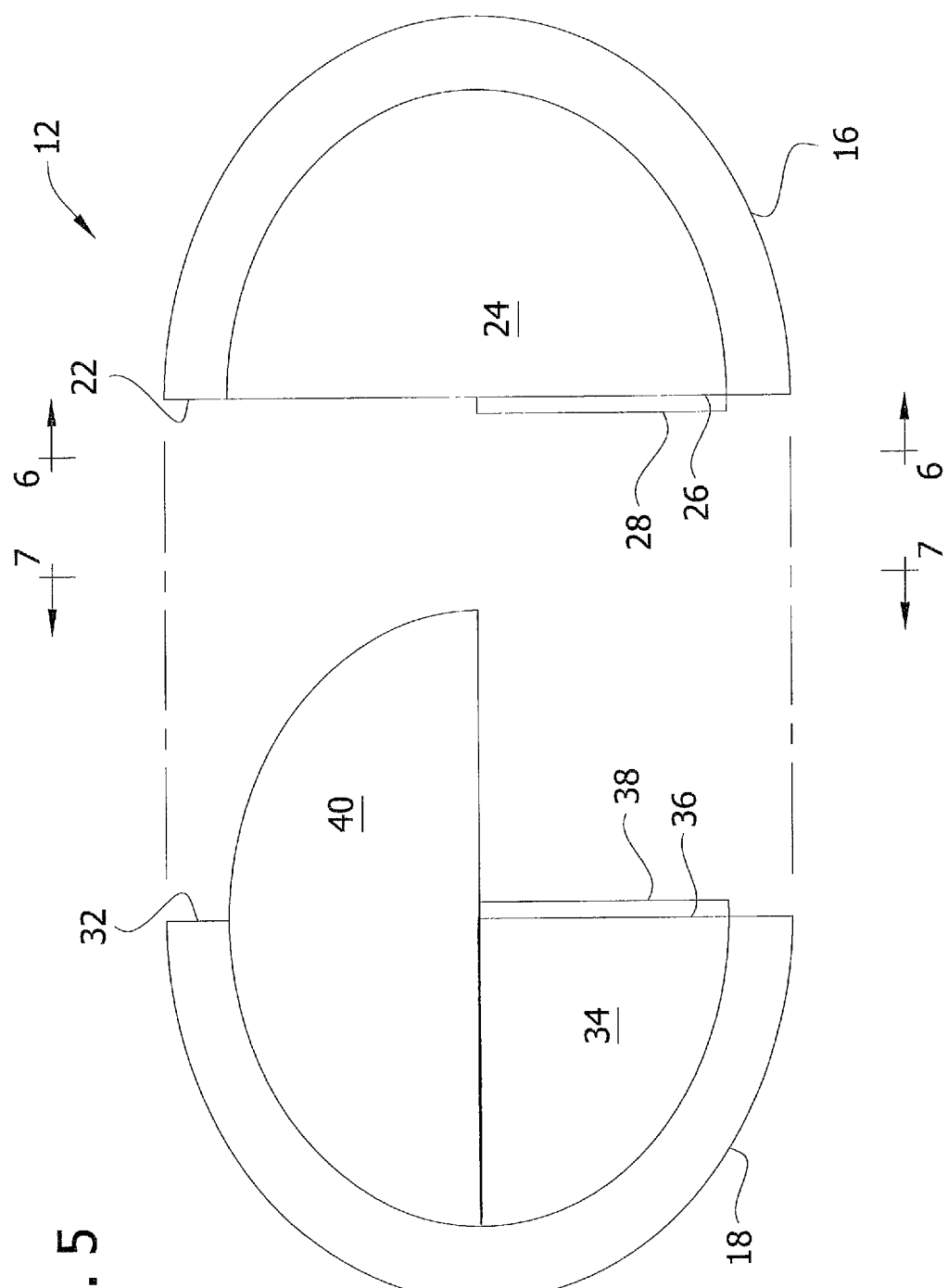
FIG. 5 is a separated top plan of the retainer assembly.
Figure 6:
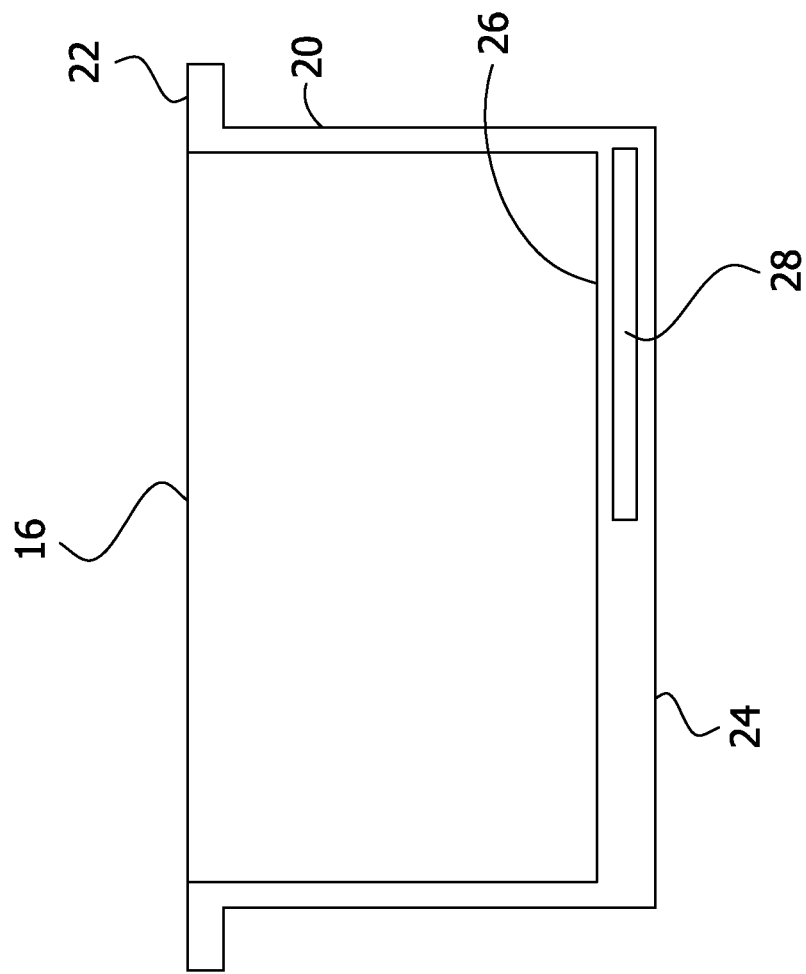
FIG. 6 is a side elevation of the retainer assembly viewed from the plane of line 6-6 of FIG. 5.

As shown in FIGS. 4 and 5, the retainer assembly 12 comprises first and second retainer elements 16, 18, respectively. The first retainer element 16, as illustrated in FIG. 6, has a shell 20 sized and shaped for extending around half of the burr hole B. Although illustrated as generally elliptical, it is envisioned the shell 20 may have other shapes such as cylindrical. The shell 20 has a flange 22 (broadly, a stop) extending around its outer end for engaging the outer table OT of the skull S to vertically position the element 16 and a plate 24 extending across its inner end that is generally aligned with the inner table IT when the flange engages the outer table. The plate 24 includes a jaw 26 extending halfway along its edge. An elastomeric insert 28 is provided on the jaw 26 for engaging the electrode E to limit damage to the electrode while holding it firmly in place.

Figure 7:
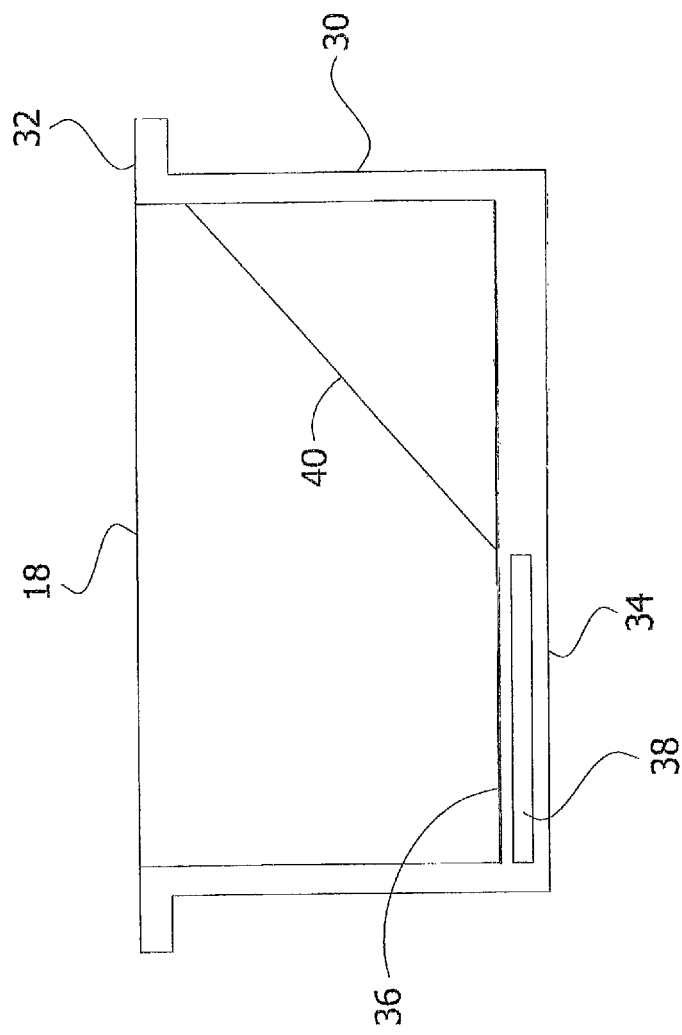
FIG. 7 is a side elevation of the retainer assembly viewed from the plane of line 7-7 of FIG. 5.

As shown in FIG. 7, the second retainer element 18 has a shell 30 sized and shaped for extending around half of the burr hole B so the second retainer element shell is shaped complementarily to the first retainer element shell 20, allowing both shells to be inserted in the burr hole B simultaneously. Although illustrated as generally elliptical, it is envisioned the shell 30 may have other shapes such as cylindrical. The second retainer element shell 30 has a flange 32 extending around its outer end for engaging the outer table OT of the skull S to vertically position the element 18. A plate 34 extends across the inner end of the second retainer element shell 30 that is generally aligned with the inner table IT when the flange 32 engages the outer table OT of the skull S. The plate 34 includes a jaw 36 extending halfway along its edge. An elastomeric insert 38 is provided on the jaw 36 for engaging the electrode E to limit damage to the electrode while holding it firmly in place. The second retainer element 18 also includes a spacer 40 extending across the plate 34 opposite the jaw 36. The spacer 40 forms a tongue that overlaps the plate 24 of the first retainer element 16 when the retainer assembly 12 is assembled in the burr hole B to interengage the first and second retainer elements 16, 18, respectively. In one embodiment illustrated in FIG. 3, the spacer 40 has a triangular shape, but it is envisioned the spacer may have other shapes without departing from the scope of the present invention. Although the retainer elements 16, 18 may be made of other biocompatible materials without departing from the scope of the present invention, in some embodiments the elements are made from extruded methy-methyacrylate or stainless steel.

As will be appreciated by those skilled in the art, the first retainer element 16 is inserted in the burr hole B so the jaw elastomeric insert 28 of the jaw 26 abuts the electrode E extending from the brain. Because the jaw 26 extends halfway across the element 16, the element may be rotated as needed so the insert 28 abuts the electrode. Thus, the offset jaw 26 accommodates the electrode E anywhere in the burr hole B regardless of its radial position in the hole from adjacent the edge of the burr hole to its center. The second retainer element 18 is inserted in the burr hole B so its elastomeric insert 38 abuts the electrode and the elastomeric insert 28 of the first retainer element 16. In this position, the spacer 40 of the second retainer element 18 overlaps part of the plate 24 of the first retainer element 16 opposite the jaw 26. The elastic components 28, 38 of the retainer elements 16, 18 are elastic enough to compress around and hold the electrode E as it emerges from the brain and enters the burr hole B at the inner table IT of the skull S.

After the electrode retainer assembly 12 is inserted in the burr hole B, the cap 14 is placed over the assembly, generally adjacent to the outer table OT of the skull as shown in FIGS. 2 and 3. The cap 14 has a smooth, convex outer surface 50 that provides a desirable low profile and smooth surface without sharp edges that could cause skin erosion. An opening 52 in the cap 14 provides an exit for the electrode E. A pair of spaced posts 54 extends downward from the cap 14 into a cavity defined by the shells 22, 32 of the first and second elements 14, 16, respectively. Lower ends of the posts 54 complement the sloped surface of the spacer 40 of the second retainer element 30 to key the opening 52 relative to the elastic components 28, 38. An edge of the opening 52 may have an elastic material 56 for engaging the electrode E to limit damage. The cap 14 may be tamped onto the retainer assembly 12 engaging a rim 60 of the cap with the flanges 22, 32 of the first and second retainer elements 16, 18. The rim 60 provides a recess for receiving the flanges 22, 32. Alternatively, the cap 14 may be secured the retainer assembly 12 in other ways. As the cap 14 is tamped in place, the retainer assembly 12 presses against a rim of the burr hole B, gently being the electrode E at the opening 52, and clamping the electrode between the cap and the retainer assembly 14, 12.

As will be apparent to those skilled in the art, the electrode clamp 10 described above allows the electrode E a generous arc to limit damage and permits the electrode to exit the clamp parallel to the skull S. The clamp 10 holds the electrode E in two places, one adjacent the inner table IT of the skull S and one adjacent the outer table OT to preserve the generous arc of the electrode. Further, the clamp 10 blocks the burr hole B to prevent loss of cerebrospinal fluid and to prevent blood from entering the intracranial space from the subgaleal space.

Moreover, the disclosed embodiment allows the electrode E to occupy a position in the burr hole B anywhere from the geometric center of the burr hole to a point in proximity to the edge of the hole. The final location of the electrode E can be determined by microelectrode recording that dictates where in the burr hole the electrode is placed. The clamp 10 is capable of clamping the electrode E at any final position the electrode emerges from the brain.

Further, the disclosed clamp 10 is configured so the outer surface of the clamp is smooth to prevent erosion of the overlying skin. This outer surface of the clamp 10 is thin to reduce the distortion of the overlying skin, and to reduce the cosmetic effects of the device on the forehead of the patient, as many patients are male with receding hairlines. Finally, the embodiment provides two clamping mechanisms on the electrode E (although the embodiment may have a single clamping mechanism inside the burr hole B adjacent to the inner table IT of the skull S) so the electrode does not move after the final position is determined in spite of drag on the electrode created by the electrode extending over the scalp and to the chest.

It should be noted that the clamp 10 may be used in other applications such as shunt procedures, catheter placement within the brain, and any procedure in which a tubular structure is inserted into the brain from outside the skull. The device described is a general purpose clamp that would satisfy the requirements for all such interventions.

Having described the invention in detail, it will be apparent that modifications and variations are possible without departing from the scope of the invention defined in the appended claims.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A clamp for clamping a brain electrode extending through a burr hole formed in a skull of a patient, the clamp comprising:
    a first retainer element having a semi-annular shell extending between an outer end and an inner end opposite the outer end, the first retainer element having a flange extending outward from an edge at the outer end of the shell of the first retainer element, the flange having a surface facing the inner end of the shell of the first retainer element for engaging an outer table of the skull, and the first retainer element having a jaw extending at least partially across the shell of the first retainer element at the inner end of the shell of the first retainer element;
    a second retainer element having a semi-annular shell shaped complementarily to the shell of the first retainer element for insertion in the burr hole simultaneously with the shell of the first retainer element, the shell of the second retainer element extending between an outer end and an inner end opposite the outer end, the second retainer element having a flange extending outward from an edge at the outer end of the shell of the second retainer element and including an inner face facing the inner end of the shell of the second retainer element for engaging the outer table of the skull, and the second retainer element having a jaw extending at least partially across the shell of the second retainer element at the inner end of the shell of the second retainer element for cooperating with the jaw of the first retainer element to clamp the electrode, the second retainer element having a spacer extending across the inner end of the shell of the second retainer element in a fixed orientation with respect to the shell of the second retainer element and overlying the first retainer element when assembled, said spacer having an outer surface facing the outer end of the shell of the second retainer element, at least a portion of the outer surface of the spacer extending obliquely relative to the inner face of the flange of the second retainer element; and
    a cap fastened to the first and second retainer elements and maintaining the jaws of the first and second retainer elements in cooperation to clamp the electrode adjacent an inner table of the skull while the flanges of the first and second retainer elements engage the outer table of the skull, the cap including an opening for receiving the electrode.

2. A clamp as set forth in claim 1, wherein the opening in the cap is positioned adjacent at least one of the flanges of the first and second retainer elements when the cap is fastened to the elements for holding the electrode against movement.

3. A clamp as set forth in claim 2, wherein the opening in the cap is positioned adjacent both of the flanges of the first and second retainer elements when the cap is fastened to the elements for holding the electrode against movement.

4. A clamp as set forth in claim 1, wherein the cap includes a rim for receiving the flanges of the first and second retainer elements when the cap is fastened to the elements.

5. A clamp as set forth in claim 1, wherein the cap has a smooth outer surface for preventing erosion of scalp adjacent the cap.

6. A clamp as set forth in claim 1, further comprising:
    a first elastomeric insert positioned on the jaw of the first retainer element for engaging the electrode; and
    a second elastomeric insert for positioning on the jaw of the second retainer element for engaging the electrode.

7. A clamp as set forth in claim 1, further comprising an elastomeric element at the opening of the cap for engaging the electrode.

8. A clamp for clamping a brain electrode extending through a burr hole formed in a skull of a patient, the clamp comprising:
    a first retainer element having a semi-annular shell extending between an outer end and an inner end opposite the outer end, the first retainer element having a flange extending outward from an edge at the outer end of the shell of the first retainer element, the flange having a surface facing the inner end of the shell of the first retainer element for engaging an outer table of the skull, and the first retainer element having a jaw extending at least partially across the shell of the first retainer element at the inner end of the shell of the first retainer element;
    a second retainer element having a semi-annular shell shaped complementarily to the shell of the first retainer element for insertion in the burr hole simultaneously with the shell of the first retainer element, the shell of the second retainer element extending between an outer end and an inner end opposite the outer end, the second retainer element having a flange extending outward from an edge at the outer end of the shell of the second retainer element and including an inner face facing the inner end of the shell of the second retainer element for engaging the outer table of the skull, and the second retainer element having a jaw extending at least partially across the shell of the second retainer element at the inner end of the shell of the second retainer element for cooperating with the jaw of the first retainer element to clamp the electrode;
    a spacer extending across the inner end of the shell of the second retainer element in a fixed orientation with respect to the shell of the second retainer element and overlying a portion of the first retainer element when clamping the electrode in the burr hole, said spacer being positioned between the jaw and the flange of the second retainer element, said spacer having an outer surface facing the outer end of the shell of the second retainer element, at least a portion of the outer surface extending obliquely relative to the inner face of the flange of the second retainer element; and
    a cap having a recess for simultaneously receiving the flanges of the first retainer element and the second retainer element for maintaining the jaws of the first and second retainer elements in cooperation to clamp the electrode adjacent an inner table of the skull while the flanges of the first and second retainer elements engage the outer table of the skull, the cap including an opening for receiving the electrode, the opening being positioned adjacent at least one of the flanges of the first and second retainer elements when the cap recess receives the flanges thereby holding the electrode against movement within the shells of the first and second retainer elements and maintaining a curvature of the electrode during use.

9. A clamp as set forth in claim 8, further comprising:

a first elastomeric insert positioned on the jaw of the first retainer element for engaging the electrode; and a second elastomeric insert for positioning on the jaw of the second retainer element for engaging the electrode.

10. A clamp as set forth in claim 8, wherein:

the jaw of the first retainer element extends partially across the first retainer element; and the jaw of the second retainer element extends partially across the second retainer element.

11. A clamp as set forth in claim 10, wherein:

the jaw of the first retainer element extends halfway across the first retainer element; and the jaw of the second retainer element extends halfway across the second retainer element.

12. A clamp as set forth in claim 8, wherein:

the shell of the first retainer element is sized to extend halfway around the burr hole; and the shell of the second retainer element is sized to extend halfway around the burr hole.

\* \* \* \* \*